(12) United States Patent
Christofidou-Solomidou et al.

(10) Patent No.: US 11,071,746 B2
(45) Date of Patent: Jul. 27, 2021

(54) COMPOSITIONS AND METHODS FOR PROTECTING ORGANS FROM ISCHEMIA/REPERFUSION INJURY ASSOCIATED WITH TRANSPLANTATION

(71) Applicant: THE TRUSTEES OF THE UNIVERSITY OF PENNSYLVANIA, Philadelphia, PA (US)

(72) Inventors: Melpo Christofidou-Solomidou, Eagleville, PA (US); Edward Cantu, Ardmore, PA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 106 days.

(21) Appl. No.: 16/308,384

(22) PCT Filed: Jun. 5, 2017

(86) PCT No.: PCT/US2017/035960
§ 371 (c)(1),
(2) Date: Dec. 7, 2018

(87) PCT Pub. No.: WO2017/214039
PCT Pub. Date: Dec. 14, 2017

(65) Prior Publication Data
US 2019/0134071 A1    May 9, 2019

Related U.S. Application Data

(60) Provisional application No. 62/347,038, filed on Jun. 7, 2016.

(51) Int. Cl.
| A61K 31/7032 | (2006.01) |
| A61P 39/00 | (2006.01) |
| A61K 31/7034 | (2006.01) |
| A61K 36/55 | (2006.01) |
| A61K 9/00 | (2006.01) |
| A61K 9/12 | (2006.01) |

(52) U.S. Cl.
CPC ........ *A61K 31/7034* (2013.01); *A61K 9/0019* (2013.01); *A61K 9/0078* (2013.01); *A61K 9/12* (2013.01); *A61K 31/7032* (2013.01); *A61K 36/55* (2013.01); *A61P 39/00* (2018.01)

(58) Field of Classification Search
None
See application file for complete search history.

(56) References Cited

U.S. PATENT DOCUMENTS

| 2010/0239696 A1 | 9/2010 | Christofidou-Solomidou |
| 2014/0308379 A1 | 10/2014 | Christofidou-Solomidou et al. |

FOREIGN PATENT DOCUMENTS

| JP | 2004-300098 | 10/2004 |
| WO | WO 2013/188016 A2 | 12/2013 |
| WO | WO 2015/184441 A2 | 12/2015 |

OTHER PUBLICATIONS

Mishra et al., "Synthesis and antioxidant evaluation of (S,S)- and (R,R)-secoisolariciresinol diglucosides (SDGs)" Bioorganic and Medicinal Chemistry Letters vol. 23 pp. 5325-5328 (Year: 2013).*
"Formulation", downloaded from https://www.cambridgemedchemconsulting.com/resources/formulation.html (Year: 2012).*
Dirk Van Raemdonck et al. Ex-vivo lung perfusion. Transplant International. Apr. 2014, vol. 28, pp. 643-656; abstract; p. 650, heading EVLP for donor lung repair.
Anastasia Velalopoulou et al. The Flaxseed-Derived Lignan Phenolic Secoisolariciresinol Diglucoside (SDG) Protects Non-Malignant Lung Cells from Radiation Damage. International Journal of Molecular Sciences. Dec. 2015; vol. 17, pp. 2-15; p. 2, fourth paragraph.
Steven M. Fiser et al. Ischemia-Reperfusion Injury After Lung Transplantation Increases Risk of Late Bronchiolitis Obliterans Syndrome. The Annals of Thoracic Surgery 2002, vol. 73, pp. 1041-1048; abstract; p. 1045, second column, first paragraph.

* cited by examiner

*Primary Examiner* — Eric Olson
(74) *Attorney, Agent, or Firm* — Mark S. Cohen; Pearl Cohen Zedek Latzer Baratz LLP

(57) ABSTRACT

The invention provides compositions and methods for protecting organs, such as lungs, from injury associated with transplantation. Specifically, the invention relates to secoisolaricirecinol diglucoside (SDG), including natural SDG, synthetic SDG (LGM2605), (S,S)-SDG, (R,R)-SDG and mixtures thereof, as well as related molecules, for protecting lungs from injury, such as ischemia/reperfusion injury, associated with transplantation.

23 Claims, 11 Drawing Sheets

LGM2605 INSTILLATION (200 mg/5 mL aerosolized saline)

FIGURE 3A

LGM2605 INSTILLATION (200 mg/5 mL aerosolized saline)

COMPOSITIONS AND METHODS FOR PROTECTING ORGANS FROM ISCHEMIA/REPERFUSION INJURY ASSOCIATED WITH TRANSPLANTATION

CROSS-REFERENCE TO RELATED APPLICATIONS

The subject Application is a U.S. national stage application under 37 U.S.C. 371 of PCT International Application PCT/US2017/035960, filed 5 Jun. 2017, which claims priority to U.S. Provisional Application No. 62/347,038, filed 7 Jun. 2016, the entire contents of which are hereby incorporated by reference in their entirety.

FIELD OF THE INVENTION

The invention relates to compositions and methods for protecting organs, such as lungs, from injury associated with transplantation. Specifically, the invention relates to a secoisolariciresinol diglucoside (SDG), including natural SDG, synthetic SDG (LGM2605), (S,S)-SDG, (R,R)-SDG and mixtures thereof, as well as related molecules, for protecting lungs from injury, such as ischemia/reperfusion injury, associated with transplantation.

BACKGROUND OF THE INVENTION

Lung transplantation is an established surgical option and implies that a lung with advanced chronic disease is replaced with a healthy donor lung, involving an episode of ischemia associated with stop of blood flow during lung preservation and reperfusion. Injury from ischemia-reperfusion (IR) is clinically known as primary graft dysfunction (PGD) and is a major cause of poor outcome of transplant surgery. Inflammatory and immunological injury-repair responses appear to be the mechanisms driving IR injury or PGD. Part of the inflammatory response is in the form of recruitment of polymorphonuclear neutrophils (PMNs) from the recipient's circulation and its adherence and transmigration into the transplanted (donor) lung. It seems that signals emanating from the endothelial layer of lung vessels drive the recruitment and adherence of PMN to the vessel wall, but how and when these signals are induced is not clear. Pulmonary ischemia (i.e., the stop of flow in the lung) causes the activation of an endothelial cell signaling cascade that leads to generation of reactive oxygen species (ROS). Based on these observations, once can safely conclude that lung ischemia associated with storage causes the induction of inflammatory moieties possibly via ROS.

Inflammation is a complex process regulated by numerous proinflammatory mediators such as damage-associated molecular patterns (DAMPs) and their receptors (pattern recognition receptors [PRRs]). Increase in the DAMP protein high-mobility group box 1 (HMGB1) and increased expression of its PRR, receptor for advanced glycation end products (RAGE), are critical in onset and amplification of inflammation and have been implicated in numerous inflammation pathologies including IR and endotoxemia. This HMGB1-RAGE axis is part of a coordinated response that cells use to trigger inflammatory cascades by activation of inflammasomes. Inflammasomes (multimeric protein complexes formed in response to infection or tissue damage) provide an integrated snapshot of the inflammatory state of an entire organ. Inflammasomes are pivotal in amplification of inflammation because they trigger production of cytokines and chemokines that, in turn, increase expression of adhesion molecules, causing further PMN and other immune cell adherence to the endothelium.

Accordingly, there exists a need for methods and compositions for protecting donor organs, such as lungs, from injury associated with transplantation.

SUMMARY OF THE INVENTION

In one aspect, provided herein are methods for extending the life of a donor organ prior to transplantation in a subject, the methods comprising: administering to the donor organ a composition comprising an effective amount of secoisolariciresinol diglucoside (SDG), an analog thereof, a stereoisomer thereof, a metabolite thereof, or a combination thereof. In some embodiments, the donor organ is a lung.

In another aspect, provided herein are methods for protecting or preserving a donor organ for transplantation, the methods comprising: administering to the donor organ a composition comprising an effective amount of secoisolariciresinol diglucoside (SDG), an analog thereof, a stereoisomer thereof, a metabolite thereof, or a combination thereof. In some embodiments, the donor organ is a lung.

In another aspect, provided herein are methods for preparing a donor organ for transplantation, the methods comprising: administering to the donor organ a composition comprising an effective amount of secoisolariciresinol diglucoside (SDG), an analog thereof, a stereoisomer thereof, a metabolite thereof, or a combination thereof. In some embodiments, the donor organ is a lung.

In another aspect, provided herein are methods for decreasing the likelihood of graft rejection of a donor lung for transplantation in a human patient, the methods comprising: administering to the lung a composition comprising an effective amount of secoisolariciresinol diglucoside (SDG), including natural SDG, synthetic SDG (LGM2605), (S,S)-SDG, (R,R)-SDG and mixtures thereof, as well as related molecules.

In another aspect, provided herein are methods for decreasing the likelihood of primary graft dysfunction (PGD) associated with lung transplantation in a human patient, the methods comprising: administering to the lung before it is transplanted into the patient a composition comprising an effective amount of secoisolariciresinol diglucoside (SDG), including natural SDG, synthetic SDG (LGM2605), (S,S)-SDG, (R,R)-SDG and mixtures thereof, as well as related molecules.

In another aspect, provided herein are methods of decreasing the likelihood of lung transplantation complications, such as bronchiolitis obliterans, in a human patient, the methods comprising: administering to the lung before it is transplanted a composition comprising an effective amount of secoisolariciresinol diglucoside (SDG), including natural SDG, synthetic SDG (LGM2605), (S,S)-SDG, (R,R)-SDG and mixtures thereof, as well as related molecules.

In another aspect, provided herein are compositions comprising an effective amount of a secoisolariciresinol diglucoside (SDG), including natural SDG, synthetic SDG (LGM2605), (S,S)-SDG, (R,R)-SDG and mixtures thereof, as well as related molecules. In some embodiments, the compositions are formulated to be administered to a donor organ, such as a lung, for transplantation in an amount effective to extend the life of the donor organ prior to transplantation in a subject. In some embodiments, the compositions are formulated to be administered to a donor organ, such as a lung, for transplantation in an amount effective to protect, prepare or preserve the donor organ for transplantation. In some embodiments, the compositions are formulated to be administered to a donor lung for transplantation in an amount effective to decrease the likelihood of graft or rejection primary graft dysfunction (PGD) of the donor lung in a human patient. In some embodiments, the compositions are formulated to be administered to a donor lung for transplantation in an amount effective to decrease the likelihood of lung transplantation complications, such as bronchiolitis obliterans, in a human patient.

Other features and advantages of the present invention will become apparent from the following detailed description examples and figures. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will be better understood from a reading of the following detailed description taken in conjunction with the drawings:

FIG. 4 Hemodynamic measurements in EVLP human lungs using aerosolized LGM2605 (SDG): Study design.

DETAILED DESCRIPTION OF THE INVENTION

Figure 1A:
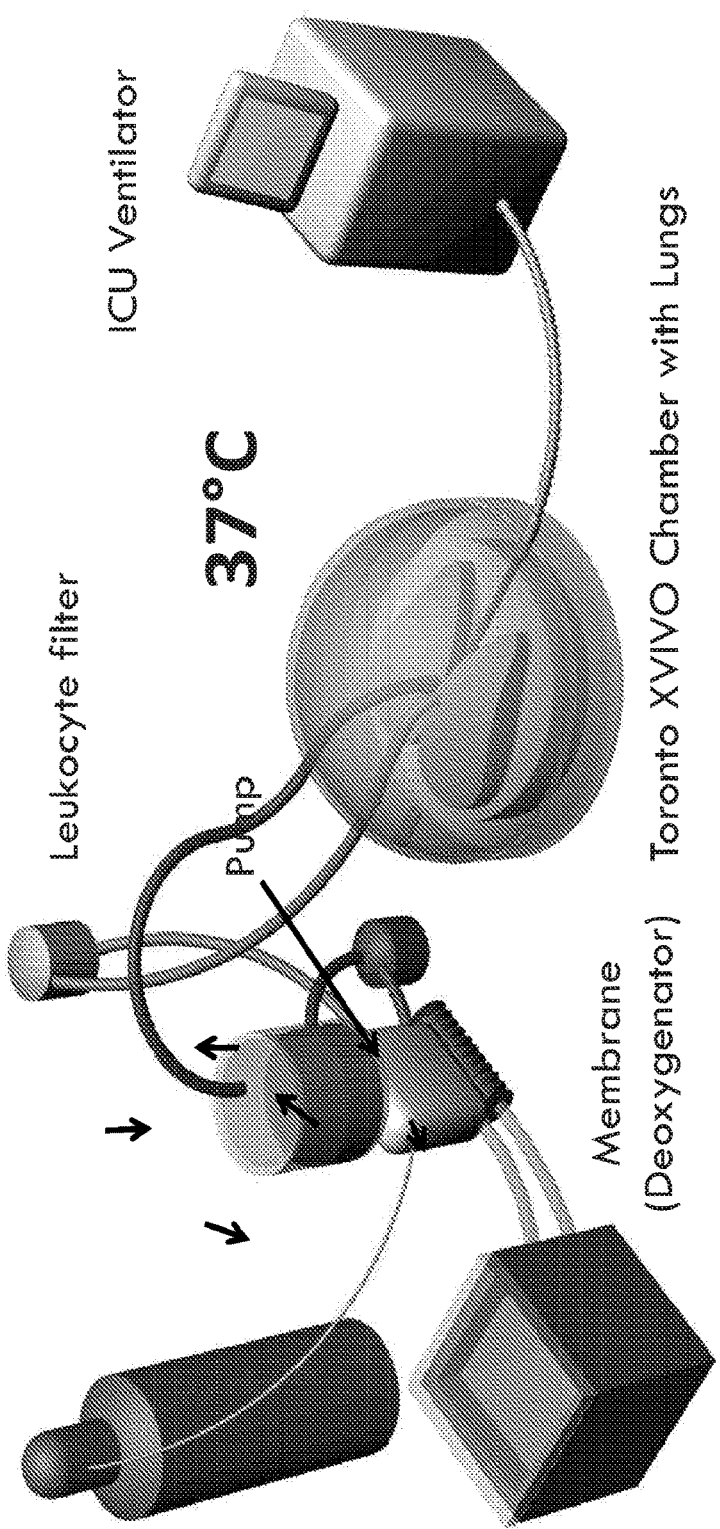
FIG. 1: Ex vivo Lung perfusion (EVLP) model system (A) in human donor lungs (B).

The invention provides compositions and methods for protecting organs, such as lungs, from injury associated with transplantation. Specifically, the invention relates to a secoisolariciresinol diglucoside (SDG), including natural SDG, synthetic SDG (LGM2605), (S,S)-SDG, (R,R)-SDG and mixtures thereof, as well as related molecules, for protecting lungs from injury, such as ischemia/reperfusion injury, associated with transplantation.

Surprisingly and unexpectedly, the inventors of this application found that SDG, including natural SDG, synthetic SDG (LGM2605), (S,S)-SDG, (R,R)-SDG and mixtures thereof, as well as related molecules, is a potent ROS scavenger and thus can be used for preventing ischemia/reperfusion (IR) injury associated with lung transplantation. The inventors have shown that SDG, including natural SDG, synthetic SDG (LGM2605), (S,S)-SDG, (R,R)-SDG and mixtures thereof, as well as related molecules, has potent anti-inflammatory and inflammasome-blocking properties and, and as a result, found that it can be used to block IR injury. The inventors also provide evidence that SDG, including natural SDG, synthetic SDG (LGM2605), (S,S)-SDG, (R,R)-SDG and mixtures thereof, as well as related molecules, can be used to extend the lung preservation period, to improve organ condition, to decrease likelihood for graft rejection, and to treat bronchiolitis obliterans (BO).

SDG is an antioxidant phytoestrogen present in flax, sunflower, sesame, and pumpkin seeds. In food, it can be found in commercial breads containing flaxseed. Flaxseed, its bioactive ingredients, and its metabolites are known in the art and described in U.S. Patent Publication Nos. 2010/0239696; 2011/0300247; and 2014/0308379; and in International Patent Publication No. WO2014/200964, each of which is incorporated by reference herein in its entirety.

The primary lignan found in flaxseed is 2,3-bis (3-methoxy-4-hydroxybenzyl) butane-1,4-diol (secoisolariciresinol or SECO), which is stored as the conjugate secoisolariciresinol diglucoside (SDG) in its native state in the plant. SDG is metabolized in the human intestine to enterodiol (ED), and enterolactone (EL). Synthetic analogs of enterodiol and enterolactone are known in the art (see, e.g., Eklund et al., *Org. Lett.*, 2003, 5:491).

Techniques for extracting and purifying SDG are known in the art and described in U.S. Pat. No. 5,705,618, which is incorporated by reference in its entirety. Techniques for synthesizing SDG, its stereoisomers and analogs are described in Mishra O P, et al., *Bioorganic & Medicinal Chemistry Letters* 2013, (19):5325-5328 and in International Patent Publication No. WO2014/200964, which are hereby incorporated by reference in their entireties. Synthetic SDG is also referred to herein as LGM2605. Bioactive components for use in the methods provided herein may also be chemically synthesized directly into the mammalian, readily metabolizable forms, Enterodiol (ED) or Enterolactone (EL), as is known in the art.

The term "metabolite," as used herein, may refer to a substance produced by metabolism or by a metabolic process. For example, a metabolite of SDG is EL or ED.

It will be appreciated by one skilled in the art that a metabolite may be a chemically synthesized equivalent of a natural metabolite.

The term "analog," as used herein, may refer to a compound whose structure is related to that of another compound. The analog may be a synthetic analog.

The terms "ingredient" or "component," as used herein, may refer to an element or a constituent in a mixture or compound.

"Pharmaceutical composition" refers to an effective amount of an active ingredient, e.g., (S,S)-SDG (R,R)-SDG, meso-SDG, SDG, SECO, EL, ED and analogs thereof, together with a pharmaceutically acceptable carrier or diluent. A "effective amount" refers to that amount which provides an effect for a given condition and administration regimen.

The compositions described herein may include an "effective amount." An "effective amount" refers to an amount effective, at quantities and for periods of time necessary, to achieve the desired result. An effective amount may vary according to factors such as the disease state, age, sex, and weight of the individual or organ, and the ability of the composition to elicit a desired response in the individual or organ. An effective amount is also one in which toxic or detrimental effects of the molecule are outweighed by the beneficial effects.

In one aspect, provided herein are methods for extending the life of a donor organ prior to transplantation in a subject, the methods comprising: administering to the donor organ a composition comprising an effective amount of secoisolaricirecinol diglucoside (SDG), an analog thereof, a stereoisomer thereof, a metabolite thereof, or a combination thereof. In some embodiments, the donor organ is a lung.

In another aspect, provided herein are methods for protecting or preserving a donor organ for transplantation, the methods comprising: administering to the donor organ a composition comprising an effective amount of secoisolaricirecinol diglucoside (SDG), an analog thereof, a stereoisomer thereof, a metabolite thereof, or a combination thereof. In some embodiments, the donor organ is a lung.

In another aspect, provided herein are methods for preparing a donor organ for transplantation, the methods comprising: administering to the donor organ a composition comprising an effective amount of secoisolaricirecinol diglucoside (SDG), including natural SDG, synthetic SDG (LGM2605), (S,S)-SDG, (R,R)-SDG and mixtures thereof, as well as related molecules. In some embodiments, the donor organ is a lung.

In another aspect, provided herein are methods for decreasing the likelihood of graft rejection of a donor lung for transplantation in a human patient, the methods comprising: administering to the lung a composition comprising an effective amount of secoisolaricirecinol diglucoside (SDG), including natural SDG, synthetic SDG (LGM2605), (S,S)-SDG, (R,R)-SDG and mixtures thereof, as well as related molecules.

In another aspect, provided herein are methods for decreasing the likelihood of primary graft dysfunction (PGD) associated with lung transplantation in a human patient, the methods comprising: administering to the lung before it is transplanted into the patient a composition comprising an effective amount of secoisolaricirecinol diglucoside (SDG), including natural SDG, synthetic SDG (LGM2605), (S,S)-SDG, (R,R)-SDG and mixtures thereof, as well as related molecules.

In another aspect, provided herein are methods of decreasing the likelihood of lung transplantation complications, such as bronchiolitis obliterans, in a human patient, the methods comprising: administering to the lung before it is transplanted a composition comprising an effective amount of secoisolaricirecinol diglucoside (SDG), including natural SDG, synthetic SDG (LGM2605), (S,S)-SDG, (R,R)-SDG and mixtures thereof, as well as related molecules.

In another aspect, provided herein are compositions comprising an effective amount of a secoisolaricirecinol diglucoside (SDG), including natural SDG, synthetic SDG (LGM2605), (S,S)-SDG, (R,R)-SDG and mixtures thereof, as well as related molecules. In some embodiments, the compositions are formulated to be administered to a donor organ, such as a lung, for transplantation in an amount effective to extend the life of the donor organ prior to transplantation in a subject. In some embodiments, the compositions are formulated to be administered to a donor organ, such as a lung, for transplantation in an amount effective to protect, prepare or preserve the donor organ for transplantation. In some embodiments, the compositions are formulated to be administered to a donor lung for transplantation in an amount effective to decrease the likelihood of graft or rejection primary graft dysfunction (PGD) of the donor lung in a human patient. In some embodiments, the compositions are formulated to be administered to a donor lung for transplantation in an amount effective to decrease the likelihood of lung transplantation complications, such as bronchiolitis obliterans, in a human patient.

In one example, an effective amount ranges from about 1 nanomolar (nM) to about 1 molar (M). In another example, an effective amount ranges from about 1 nM to about 1 mM. In another example, an effective amount is in the nanomolar to millimolar range. In yet another example, an effective amount ranges from about 1 nM to about 1 µM.

As used herein, the phrase "pharmaceutically acceptable" refers to those compounds, materials, compositions, carriers, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used herein includes both one and more than one such excipient.

Pharmaceutical compositions can be administered to a subject by any suitable method known to a person skilled in the art, such as orally, parenterally, transmucosally, transdermally, intramuscularly, intravenously, intra-dermally, subcutaneously, intra-peritonealy, intra-ventricularly, intra-cranially, intra-vaginally, intra-tumorally, or bucally. Controlled release may also be used by embedding the active ingredient in an appropriate polymer which may then be inserted subcutaneously, intratumorally, bucally, as a patch on the skin, or vaginally. Coating a medical device with the active ingredient is also covered.

In some embodiments, the pharmaceutical compositions are are formulated in a form suitable for administration as a liquid or a solid preparation. Suitable liquid formulations include aerosols, solutions, suspensions, dispersions, emulsions, oils and the like. Suitable solid formulations include tablets, capsules, pills, granules, pellets and the like. In some embodiments, the pharmaceutical compositions are administered by intravenous injection of a liquid preparation. In some embodiments, the pharmaceutical compositions are administered intravenously and are thus formulated in a form suitable for intravenous administration.

In one example, the pharmaceutical compositions provided herein are controlled-release compositions, i.e. compositions in which the flaxseed, its bioactive ingredient, or a metabolite thereof is released over a period of time after administration. Controlled- or sustained-release compositions include formulation in lipophilic depots (e.g. fatty acids, waxes, oils). In another example, the composition is an immediate-release composition, i.e. a composition in which all the flaxseed, its bioactive ingredient, or a metabolite thereof is released immediately after administration.

In some embodiments, compositions for use in the methods provided herein are administered once per day. In some embodiments, the compositions are administered once every two days, twice a week, once a week, or once every two weeks.

Natural SDG, synthetic SDG (LGM2605), (S,S)-SDG (R,R)-SDG, (S,R)-SDG (R,S)-SDG, meso-SDG, SECO, EL, ED or an analog thereof may be administered at a dose of 0.1 ng/kg to 500 mg/kg.

Treatment with Natural SDG, synthetic SDG (LGM2605), (S,S)-SDG (R,R)-SDG, (S,R)-SDG (R,S)-

SDG, meso-SDG, SDG, SECO, EL, ED or an analog thereof is a single administration to several days, months, years, or indefinitely.

As used herein, "treating" may refer to either therapeutic treatment or prophylactic or preventative measures, wherein the object is to prevent or lessen the targeted pathologic condition or disorder as described herein, or both.

Furthermore, as used herein, the terms "treat" and "treatment" refer to therapeutic treatment, as well prophylactic or preventative measures, wherein the object is to prevent or slow down (lessen) an undesired physiological change associated with a disease or condition. Beneficial or desired clinical results include, but are not limited to, alleviation of symptoms, diminishment of the extent of a disease or condition, stabilization of a disease or condition (i.e., where the disease or condition does not worsen), delay or slowing of the progression of a disease or condition, amelioration or palliation of the disease or condition, and remission (whether partial or total) of the disease or condition, whether detectable or undetectable. "Treatment" can also mean prolonging survival as compared to expected survival if not receiving treatment.

In some embodiments, subjects in need of treatment and the methods and compositions described herein may include, but are not limited to, subjects with lung diseases and disorders, such as asthma, cancer, COPD, and mesothelioma. In one exemplary embodiment, the subject is a patient who is in need of a lung transplantation. In another exemplary embodiment, the subject is a patient who is waiting for a lung transplantation. In another exemplary embodiment, the subject is a patient who expects to have a lung transplantation.

The term "subject" includes mammals, e.g., humans, companion animals (e.g., dogs, cats, birds, and the like), farm animals (e.g., cows, sheep, pigs, horses, fowl, and the like) and laboratory animals (e.g., rats, mice, guinea pigs, birds, and the like). In addition to humans, the subject may include dogs, cats, pigs, cows, sheep, goats, horses, buffalo, ostriches, guinea pigs, rats, mice, birds (e.g., parakeets) and other wild, domesticated or commercially useful animals (e.g., chicken, geese, turkeys, fish). The term "subject" does not exclude an individual that is normal in all respects. The term "subject" includes, but is not limited to, a human in need of therapy for, or susceptible to, a condition or its sequelae.

The term "about" or "approximately" means within an acceptable error range for the particular value as determined by one of ordinary skill in the art, which will depend in part on how the value is measured or determined, i.e., the limitations of the measurement system.

All patents, patent applications, and scientific publications cited herein are hereby incorporated by reference in their entirety.

The following examples are presented in order to more fully illustrate the preferred embodiments of the invention. They should in no way be construed, however, as limiting the broad scope of the invention.

EXAMPLES

SDG Protects Organs from Ischemia/Reperfusion Injury Associated with Transplantation Pulmonary transplantation has made considerable progress these last twenty years with a doubling of survival rates for certain indications, such as cystic fibrosis. These improvements encourage physicians to propose early lung transplantation to their patients. Contrary to other organs, like the kidneys or liver, lungs are harvested in only 20% of brain-dead donors due to very strict criteria for acceptance of lung grafts for a possible transplantation. This severe selection is motivated by high mortality rates after lung transplantation, which remained around 50% for the first five years. Several strategies have been implemented to try to increase the number of available lung grafts. Organ procurement from living donors remains anecdotal. Certain teams transplant lungs with extended criteria even though these lungs had at first been rejected due to chest X-ray abnormalities, age>70 years, poor oxygenation, or aspiration without ex vivo evaluation procedures. In many is instances, this situation has had no apparent detrimental effect on post-transplant outcome. There is, however, some evidence that extension of donor acceptability in some respects leads to poorer early outcomes, mainly by increasing the rate of early graft dysfunction.

Ex vivo Lung perfusion (EVLP) evaluates these "marginal" lungs outside of the body, thus allowing a more objective and reproducible assessment of these organs. Beyond the ex vivo evaluation, EVLP may prolong the lung preservation period for up to 12 h. Promising research has suggested that the protection or repair of injured grafts might be performed during EVLP by delivering therapies during the procedure. We provide evidence that LGM2605 (SDG) can serve as such therapy and can thus, be useful to extend the lung preservation period as well as improve organ condition decreasing likelihood for graft rejection and further chronic complications such as bronchiolitis obliterans (BO).

Ex Vivo Lung Graft Perfusion Study Design

Figure 1B:
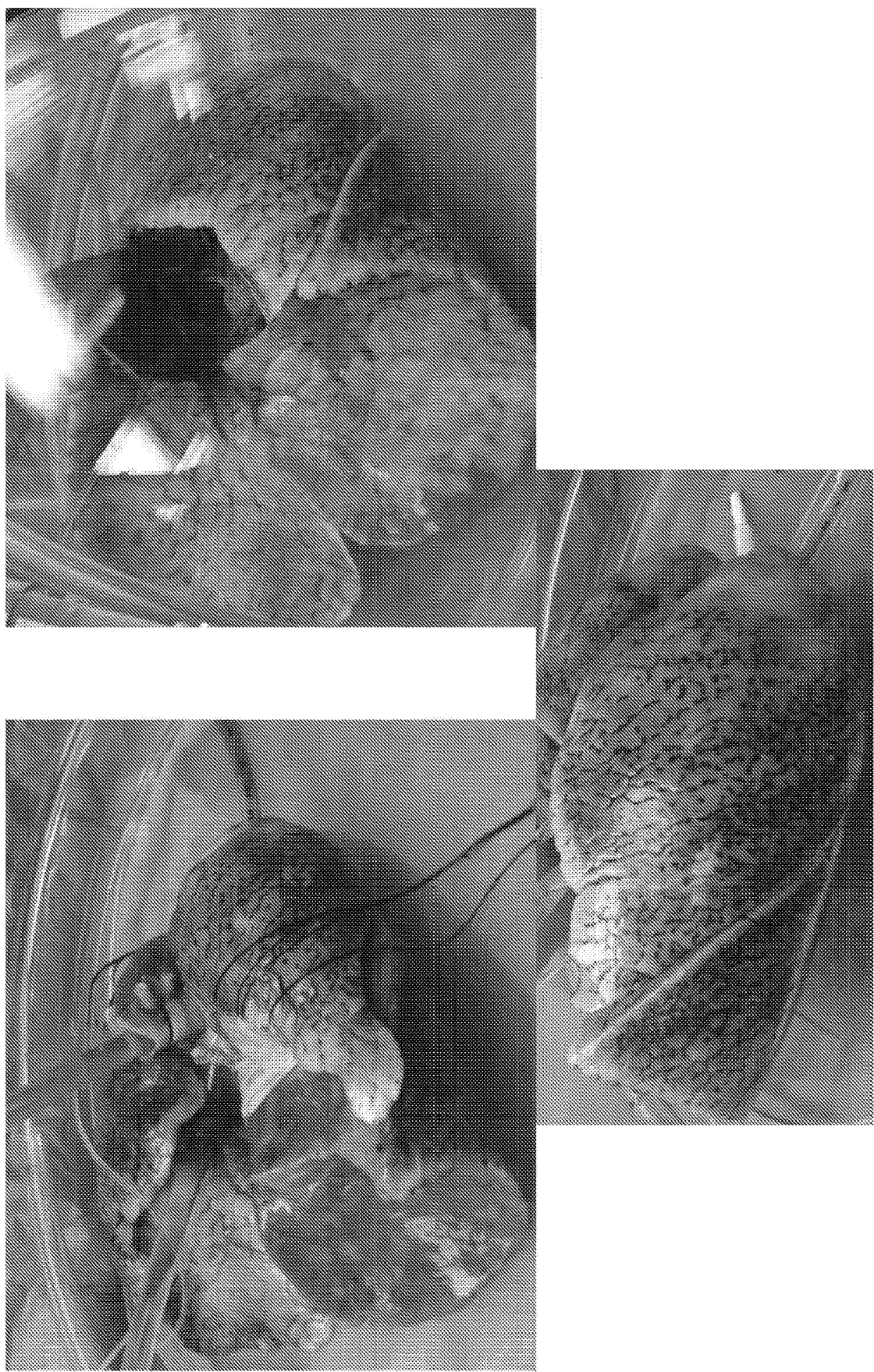

Donor lungs were offered to our lung-transplantation program through our local organ procurement organization (Gift of Life) and were de-identified. Donor lungs that met the entry criteria (i.e., non-transplantable) were retrieved, delivered to our center by means of standard cold-storage transport in a low-potassium dextran solution (Perfadex, Vitrolife), and perfused in the EVLP system for 3-6 hours. Lungs were considered suitable for transplantation if during EVLP the $PO_2:FIO_2$ ratio—that is, the partial pressure of oxygen ex vivo ($PO_2$) to the fraction of inspired oxygen ($FIO_2$)—was 350 mm Hg or more and if deterioration from baseline levels of all three physiological measurements (pulmonary vascular resistance, dynamic compliance, and peak inspiratory pressure) was less than 15% while the lungs were ventilated with the use of a tidal volume of 7 ml per kilogram of donor body weight and a rate of 7 breaths per minute during the perfusion period (FIG. 1)

Technique: The acellular EVLP technique has been described in detail elsewhere (Cypel et al., N Engl J Med. 2011 Apr. 14; 364(15):1431-40). After 3-6 hours of EVLP, the lungs were cooled to 4° C. over a period of 10 minutes. Thereafter, perfusion and ventilation were stopped (with $FIO_2$ changed to 0.21 for the purpose of lung storage), and the trachea was clamped at full inspiration to maintain the lungs in a state of inflation. The lungs were then stored at 4° C. in Perfadex until transplantation.

Ex Vivo Functional Assessment: For the functional assessment ex vivo, tidal volume was set at 10 ml per kilogram of donor body weight and 10 breaths per minute, with $FIO_2$ at 1.0. Lung function was evaluated hourly during EVLP according to the following calculations: $PO_2$=[left atrial $PO_2$–pulmonary-artery $PO_2$ (in mm Hg)], and pulmonary vascular resistance=[(pulmonary-artery pressure-left atrial pressure)×80]÷pulmonary-artery flow (in dynes·seconds·cm$^{-5}$), dynamic compliance (in milliliters per centimeter of water), and peak inspiratory pressure (in centimeters of water). Flexible bronchoscopy was performed at baseline, 3 hours and 6 hours of EVLP.

Figure 2:
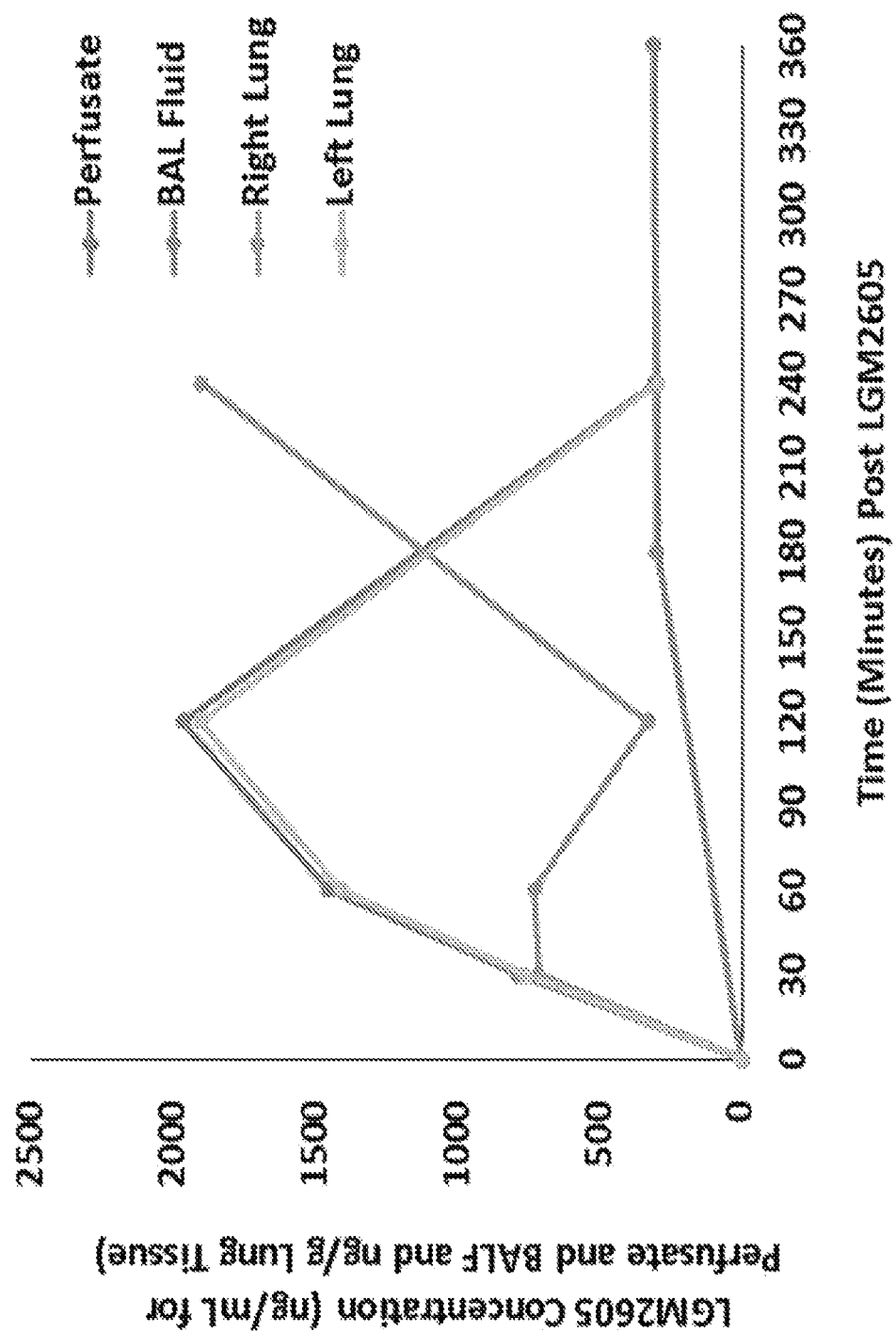
FIG. 2: LGM2605 administered via nebulizer to human donor lungs in an EVLP system can be detected in BALF, perfusate and lung tissue using LC/MS/MS for several hours.

LGM2605 (SDG) ACCUMULATES IN HUMAN LUNG TISSUES: Using LC/MS/MS analytical methodologies, we determined synthetic SDG (LGM2605) levels in left and right lung tissues, in bronchoalveolar lavage fluid (BALF) and perfusate fluid over multiple time points spanning from 30 minutes post aerosolized instillation of 200 mg drug/lung, to 360 minutes (FIG. 2). Of importance is that aerosolized SDG (LGM2605) (i.e, instilled in airways), leaks into the systemic circulation and can be detected in the perfusate for at least 240 minutes. Importantly, levels in lung tissue biopsies show a peak of drug by 120 minutes, persisting for up to 240 minutes. Additionally, levels in BALF persist beyond 360 min. Regardless of route of delivery (inhaled or intravenous), SDG (LGM2605) accumulates in lung.

Figure 3B:
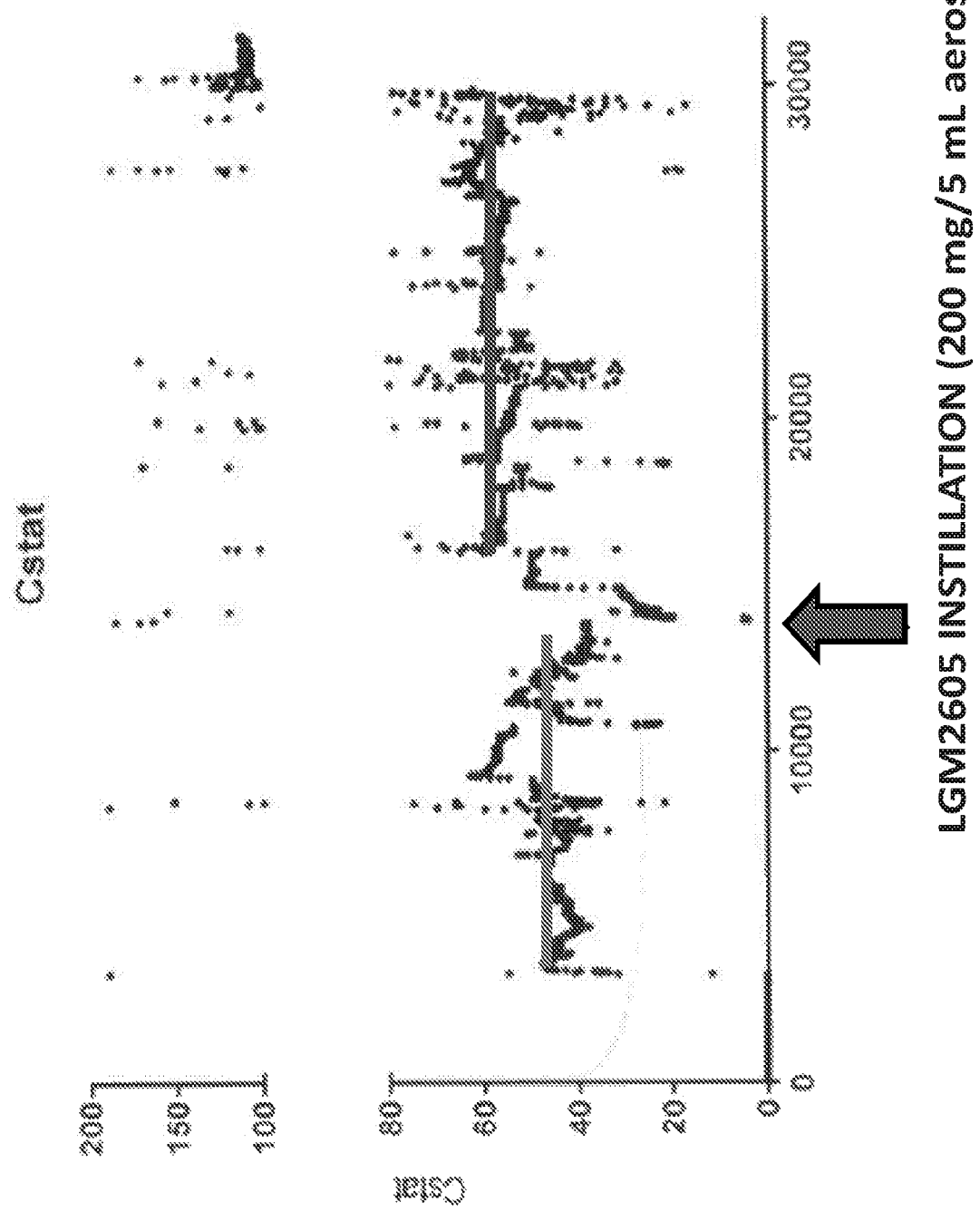
FIG. 3: Hemodynamic measurements in EVLP human lungs. LGM2605 administered via nebulizer to human donor lungs in an EVLP system improves oxygenation (P/F ratio) (FIG. 3A), static compliance (FIG. 3B), and dynamic compliance (FIG. 3C).

LGM2605 (SDG) IMPROVES LUNG OXYGENATION AND COMPLIANCE: Aerosolized drug (SDG (LGM2605)) from the same lung as above (EVLP #3) improved P/F ratio from 200 to >350 (FIG. 3, 1$^{st}$ panel), while improving dynamic (middle) and static compliance (last panel). SDG has thus improved lung hemodynamic measurements within minutes of instillation into EVLP lungs.

Figure 4:
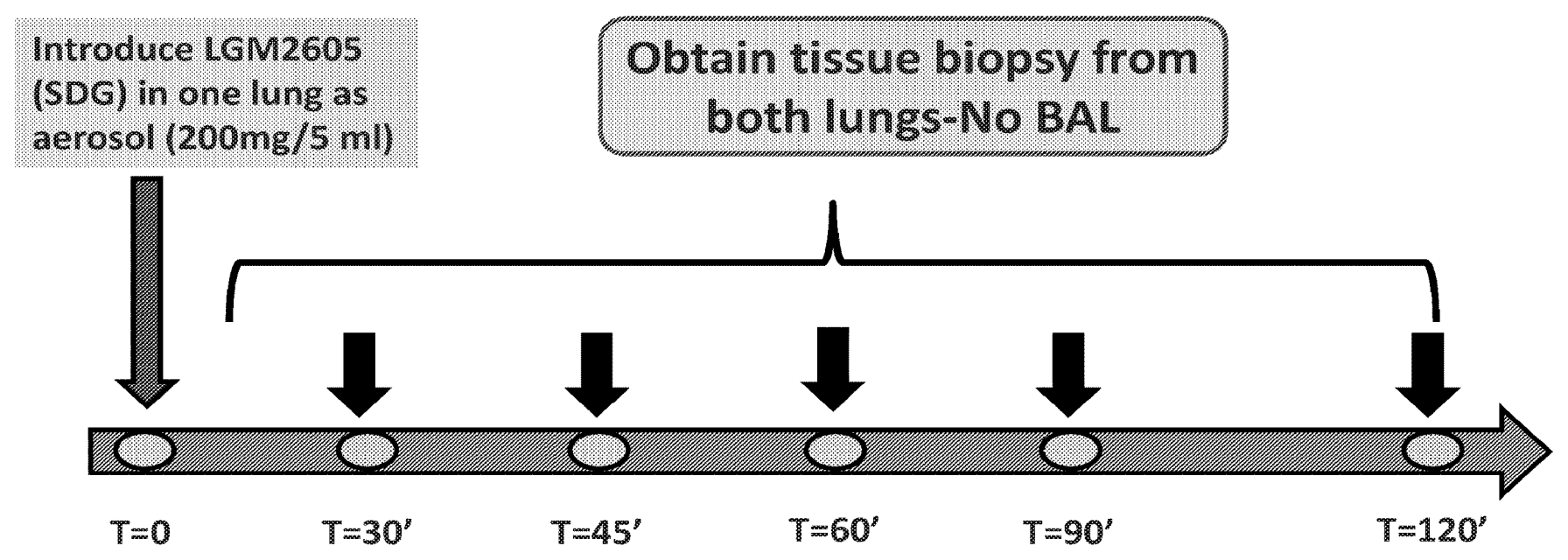
Figure 5:
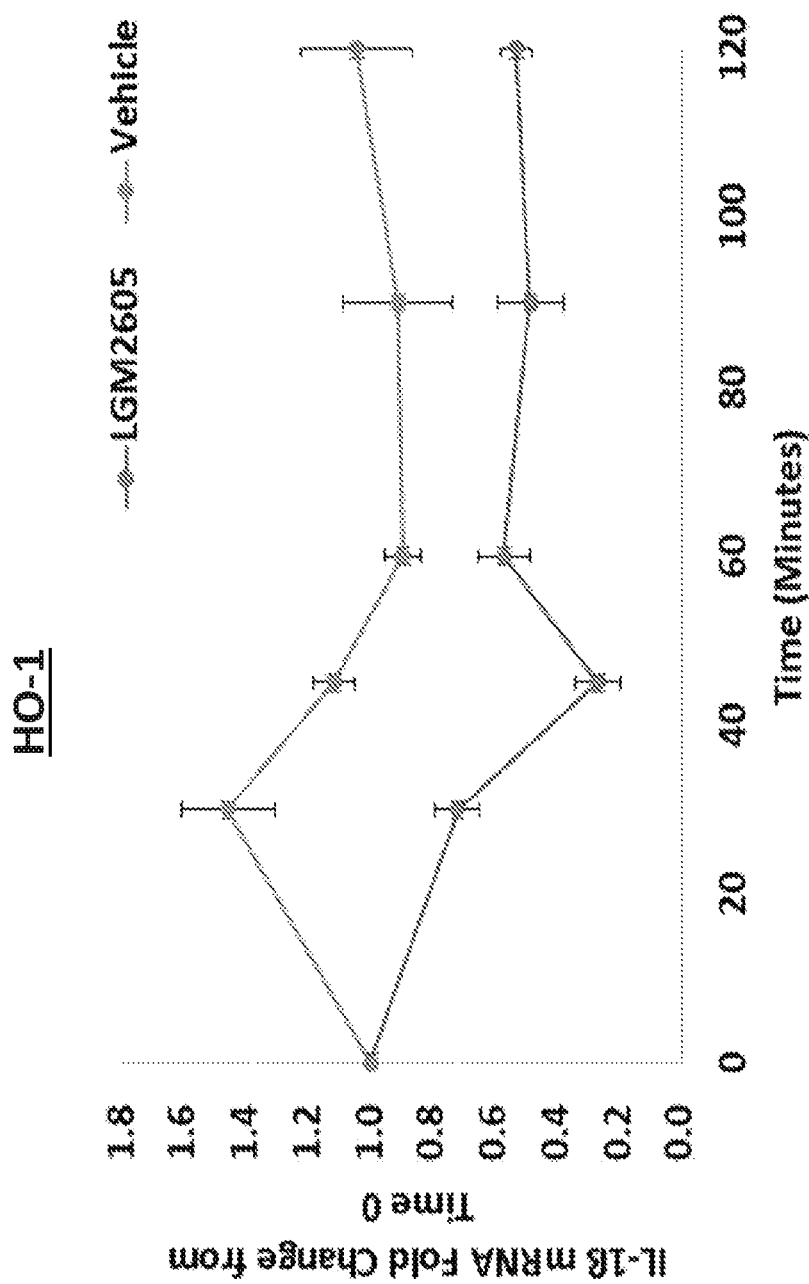
FIG. 5: Gene expression level of the NRF2-regulated stress response enzyme HO-1 decreases in human lung (EVLP) tissues treated with aerosolized LGM2605. Time "0" is the time of aerosol administration of LGM2605.

GENE EXPRESSION LEVEL OF THE NRF2-REGULATED STRESS RESPONSE ENZYME HO-1: In a separate study (EVLP #4), SDG (LGM2605) was instilled only in one lung (right) while vehicle control was instilled in the contralateral lung (FIG. 4). The concentration of the drug (200 mg/lung) was kept the same as above. Analysis of the kinetics of gene expression changes in EVLP lung tissues using quantitative RT-PCR (qRT-PCR) revealed a drop in hemeoxygenase-1 (HO-1), a stress response gene, in the lung that was associated with SDG (LGM2605) instilled in that lung (FIG. 5). A drop in the left lung may reflect action of SDG (LGM2605) on that lung through the perfusate (we have shown above that some of the drug appears into the systemic circulation).

Figure 6:
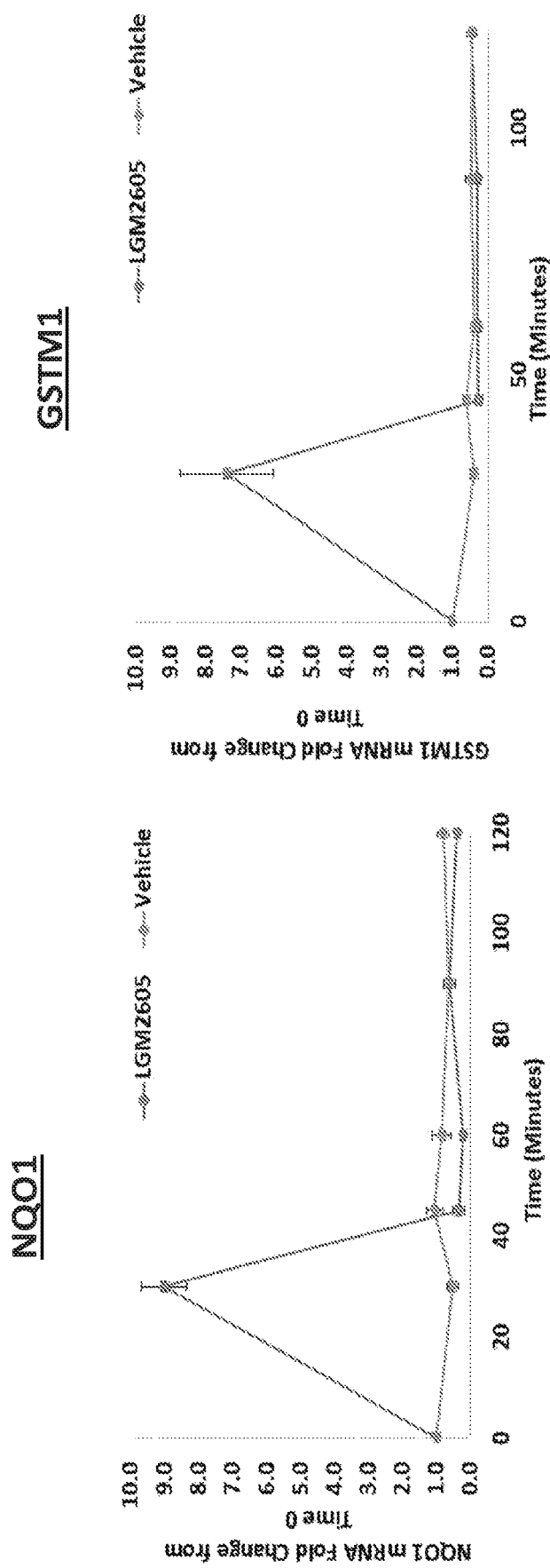
FIG. 6: Gene expression levels of the NRF2-regulated antioxidant enzymes NQO1 and GSTM1 increase in human lung (EVLP) tissues treated with LGM2605. Time "0" is the time of aerosol administration of SDG.

GENE EXPRESSION LEVELS OF THE NRF2-REGULATED ANTIOXIDANT ENZYMES NQO1 AND GSTM1 INCREASE IN HUMAN LUNG (EVLP) TISSUES TREATED WITH LGM2605 (SDG): Nrf2 is a transcription factor that regulates the expression of antioxidant and cytoprotective genes such as NQO-1 and GSTMu1. We therefore, evaluated gene expression levels in lung tissues (EVLP #4) over a 120' sampling time. qRT-PCR analysis revealed a robust increase in the expression of both genes in the lung treated with SDG (LGM2605), but not in the vehicle-treated lung. Our findings confirm that SDG boosts endogenous antioxidant defenses in human lung tissues during ischemia (FIG. 6).

Figure 7:
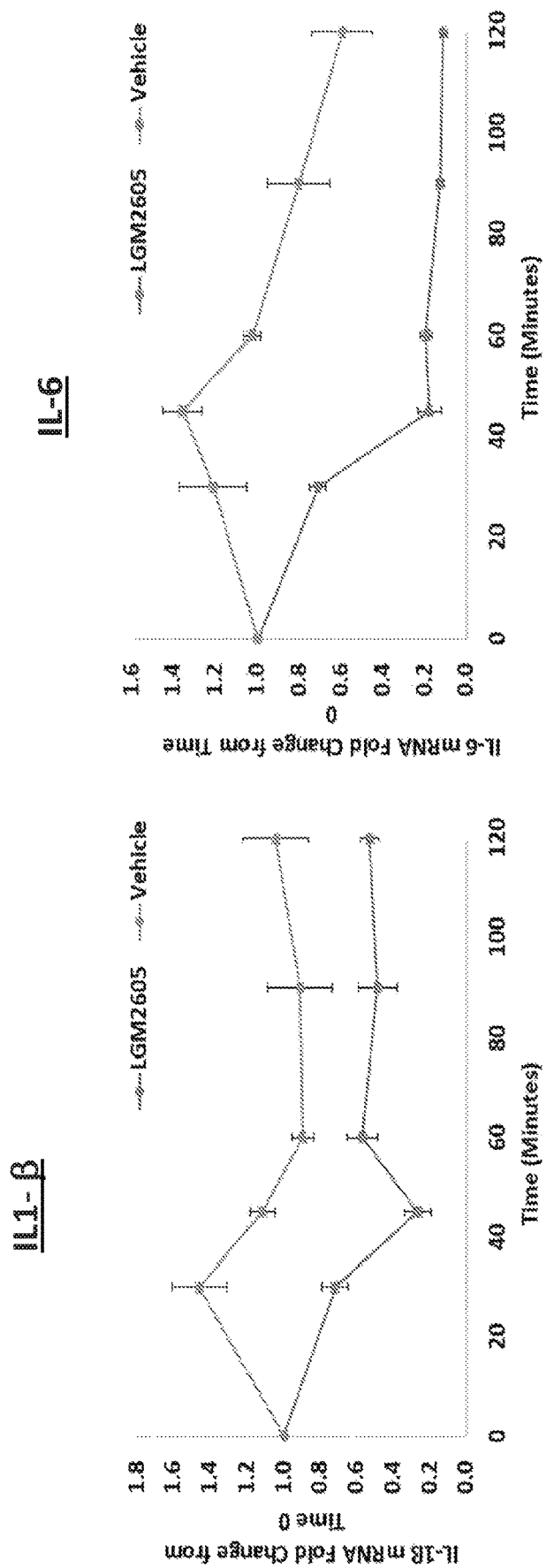
FIG. 7: Gene expression levels of pro-inflammatory cytokines IL1-β and IL-6 decrease in human lung (EVLP) tissues treated with LGM2605.

GENE EXPRESSION LEVELS OF PRO-INFLAMMATORY CYTOKINES IL1-b AND IL-6 DECREASE IN HUMAN LUNG (EVLP) TISSUES TREATED WITH LGM2605 (SDG): Similarly as above, expression levels of pro-inflammatory cytokines such as IL-1β and IL-6 was significantly reduced in the right lung, treated with SDG (LGM2605) as opposed to the vehicle-treated ling (FIG. 7). Our findings confirm that SDG decreases inflammatory parameters in human lung tissues during ischemia.

Figure 8:
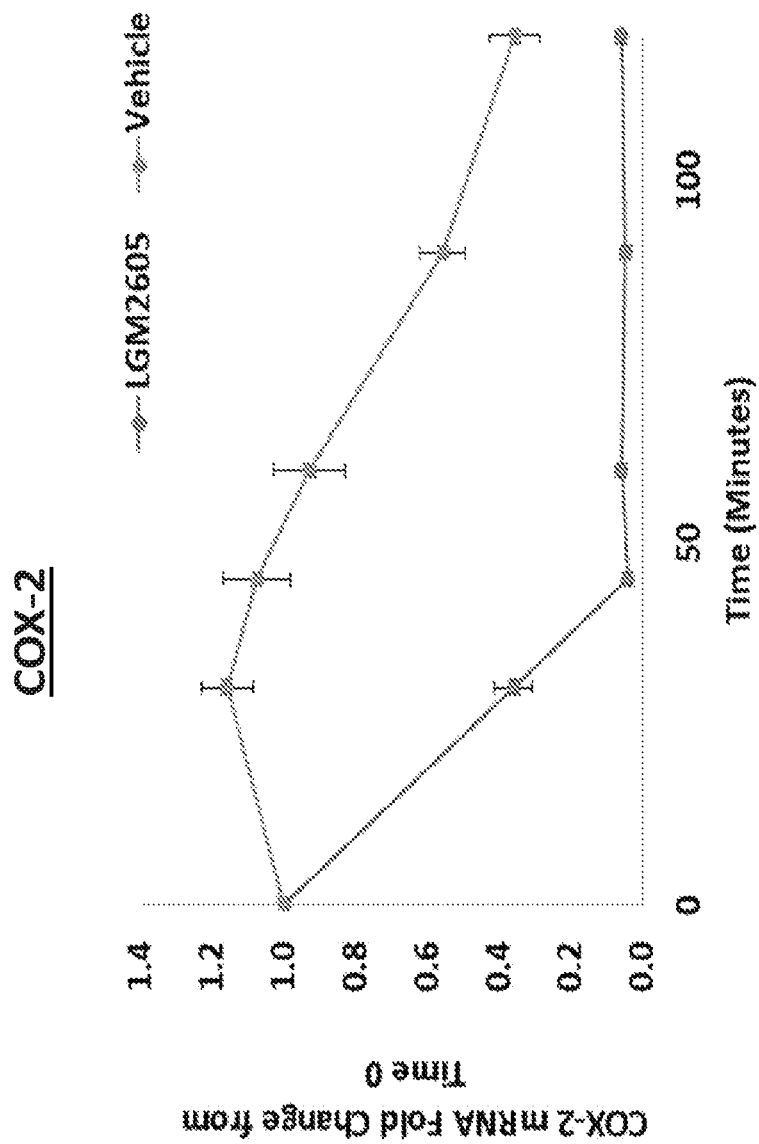
FIG. 8: Gene expression levels of COX-2 (an enzyme promoting inflammation and pain) decrease in human lung (EVLP) tissues treated with LGM2605.

GENE EXPRESSION LEVELS OF THE COX-2 (AN ENZYME PROMOTING INFLAMMATION AND PAIN) DECREASE IN HUMAN LUNG (EVLP) TISSUES TREATED WITH LGM2605 (SDG): Cyclo-oxygenease-2 is an enzyme responsible for the formation of prostanoids such as thromboxane and prostanglandins. Pharmacological inhibition of COX can provide relief from symptoms of inflammation and pain. Aerosolized instillation of SDG (LGM2605) blocks entirely the expression of COX-2 in human EVLP lung tissues within 50 minutes of instillation. A drop in the vehicle-treated lung may reflect action of the drug via the perfusate (systemic circulation—FIG. 8).

SUMMARY OF FINDINGS: Collectively, these findings show that SDG (LGM2605): Accumulates in human lung tissues during EVLP; improves human lung hemodynamics (P/F ratio, dynamic and static compliance); decreases oxidative stress (HO1); Boosts tissue antioxidant defenses (NQO-1 and GSTMu1); Decreases inflammatory markers (IL-1β and IL-6); Decreases COX-2 expression.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. An ex vivo method of protecting or preserving a lung for transplantation, the method comprising: during ex vivo lung perfusion (EVLP), administering to the lung a composition comprising an effective amount of secoisolaricirecinol diglucoside (SDG).

2. The method of claim 1, wherein said SDG is (S,S)-SDG.

3. The method of claim 1, wherein said SDG is (R,R)-SDG.

4. The method of claim 1, wherein said SDG is a synthetic SDG (LGM2605).

5. The method of claim 1, wherein the composition is administered with a nebulizer.

6. The method of claim 1, wherein the composition is administered in the form of an aerosol.

7. The method of claim 1, wherein the composition is administered intravenously.

8. The method of claim 1, wherein the SDG is administered as a saline solution.

9. The method of claim 1, wherein the SDG is administered in a concentration in a nanomolar (nM) to millimolar (mM) range.

10. The method of claim 1, wherein the lung is a human lung.

11. The method of claim 1, further comprising the step of assessing the lung for transplantation into a subject.

12. An ex vivo method for extending the life of a donor lung prior to transplantation in a subject, the method comprising: during ex vivo lung perfusion (EVLP), administering to the donor lung a composition comprising an effective amount of secoisolaricirecinol diglucoside (SDG).

13. The method of claim 12, wherein said SDG is (S,S)-SDG.

14. The method of claim 12, wherein said SDG is (R,R)-SDG.

15. The method of claim 12, wherein said SDG is a synthetic SDG (LGM2605).

16. The method of claim 12, wherein the composition is administered with a nebulizer.

17. The method of claim 12, wherein the composition is administered in the form of an aerosol.

18. The method of claim 12, wherein the composition is administered intravenously.

19. The method of claim 12, wherein the SDG is administered as a saline solution.

20. The method of claim 12, wherein the SDG is administered in a concentration in a nanomolar (nM) to millimolar (mM) range.

21. The method of claim 12, wherein the subject is a human.

22. The method of claim 12, further comprising the step of assessing the donor organ for transplantation into the subject.

23. An ex vivo method for decreasing the likelihood of graft rejection of a donor lung for transplantation in a human patient, the method comprising: during ex vivo lung perfusion (EVLP), administering to the lung a composition comprising an effective amount of secoisolaricirecinol diglucoside (SDG).

\* \* \* \* \*